(12) United States Patent
Guo et al.

(10) Patent No.: US 12,180,304 B2
(45) Date of Patent: Dec. 31, 2024

(54) VARIABLE REGION SEQUENCE OF BROAD-SPECTRUM ANTIBODY AGAINST CLOTHIANIDIN AND DINOTEFURAN AND PREPARATION OF INTACT RECOMBINANT ANTIBODY THEREOF

(71) Applicant: Zhejiang University, Zhejiang (CN)

(72) Inventors: Yirong Guo, Zhejiang (CN); Yunyun Chang, Zhejiang (CN); Ying Zhao, Zhejiang (CN); Pengyan Liu, Zhejiang (CN); Ying Liu, Zhejiang (CN); Yang Chen, Zhejiang (CN); Guonian Zhu, Zhejiang (CN)

(73) Assignee: Zhejiang University, Hangzhou (CN)

( * ) Notice: Subject to any disclaimer, the term of this patent is extended or adjusted under 35 U.S.C. 154(b) by 772 days.

(21) Appl. No.: 17/443,888

(22) Filed: Jul. 28, 2021

(65) Prior Publication Data
US 2022/0033524 A1    Feb. 3, 2022

(30) Foreign Application Priority Data

Jul. 28, 2020   (CN) .......................... 202010736532.7

(51) Int. Cl.
*C07K 16/44*    (2006.01)

(52) U.S. Cl.
CPC .......... *C07K 16/44* (2013.01); *C07K 2317/20* (2013.01); *C07K 2317/64* (2013.01)

(58) Field of Classification Search
CPC ................ C07K 16/44; C07K 2317/20; C07K 2317/64
See application file for complete search history.

(56) References Cited

U.S. PATENT DOCUMENTS

| | | | |
|---|---|---|---|
| 9,090,679 B2 * | 7/2015 | Yokoseki | A61P 43/00 |
| 11,884,743 B2 * | 1/2024 | Guo | G01N 33/54387 |
| 2018/0326027 A1 * | 11/2018 | Cashman | C07K 7/06 |

FOREIGN PATENT DOCUMENTS

JP    4841856 B2 * 12/2011

OTHER PUBLICATIONS

Winkler et al. Journal of Immunology (2000) 165(8): 4505-4514. (Year: 2000).*
Edwards et al. Journal of Molecular Biology (2003) 334(1):103-118. (Year: 2003).*
Lloyd et al. Protein Engineering, Design and Selection (2009) 22(3): 159-168. (Year: 2009).*
Schroeder and Cavacini. Journal of Allergy and Clinical Immunology (2010) 125(2, Suppl.2): S41-S52. (Year: 2010).*
Uchigashima et al. Sensors (2012) 12(11): 15858-15872. (Year: 2012).*
Sela-Culang et al. Frontiers in Immunology (2013) 4: 302. (Year: 2013).*
Li et al. Agricultural and Food Chemistry (2013) 61(15): 3561-3762. (Year: 2013).*

* cited by examiner

*Primary Examiner* — Brad Duffy
*Assistant Examiner* — Elizabeth A Shupe
(74) *Attorney, Agent, or Firm* — Lowenstein Sandler LLP

(57) ABSTRACT

The present disclosure provides a variable region sequence of a broad-spectrum antibody against clothianidin and dinotefuran, where a gene encoding a heavy chain variable region has an amino acid sequence shown in SEQ ID NO: 2. The present disclosure further discloses a broad-spectrum intact recombinant antibody against clothianidin and dinotefuran, including a heavy chain constant region, a heavy chain variable region, a light chain constant region, and a light chain variable region, where a gene encoding the heavy chain variable region has an amino acid sequence shown in SEQ ID NO: 2. The sequence genes obtained by the present disclosure are ligated to an expression vector containing a heavy chain constant region gene and a light chain constant region gene, respectively, and an intact recombinant antibody is expressed and obtained by using mammalian cells with a double-plasmid system.

9 Claims, 2 Drawing Sheets

Specification includes a Sequence Listing.

VARIABLE REGION SEQUENCE OF BROAD-SPECTRUM ANTIBODY AGAINST CLOTHIANIDIN AND DINOTEFURAN AND PREPARATION OF INTACT RECOMBINANT ANTIBODY THEREOF

CROSS REFERENCE TO RELATED APPLICATION(S)

This patent application claims the benefit and priority of Chinese Patent Application No. 202010736532.7, filed on Jul. 28, 2020, the disclosure of which is incorporated by reference herein in its entirety as part of the present application.

TECHNICAL FIELD

The present disclosure belongs to the technical field of genetic engineering, and particularly relates to a preparation method and use of a broad-spectrum intact recombinant antibody against clothianidin and dinotefuran.

BACKGROUND ART

Clothianidin is a second-generation neonicotinoid insecticide. Because there is a thiazole ring group, clothianidin has more outstanding performance than traditional nicotinic insecticides. As an efficient and broad-spectrum neonicotinoid, clothianidin has been a worldwide large-scale insecticide over the past few years, so that the consumption and sales thereof have been maintained at a high level every year. Studies on the toxicity of clothianidin to non-target organisms and its effect on the safety of ecological environment have aroused widespread concern. In the past two years, many countries worldwide have introduced policies to restrict the use of clothianidin. The European Union (EU) has now banned the use of clothianidin in outdoor environments. In EU standards, the maximum residue limits (MRLs) of clothianidin in different foods are 0.01-1.5 mg/kg. In China, the MRLs of clothianidin are set at 0.02-2 mg/kg.

Dinotefuran, as a third-generation neonicotinoid insecticide, is quite different from other common neonicotinoid insecticides in the chemical structure. A tetrahydrofuran group replaces the previous chloropyridyl or chlorothiazolyl group, and there is no halogen element.

Furthermore, there is a difference in performance, including wider insecticidal spectrum, long-lasting efficacy, and better control effects on pests that have developed resistance to traditional neonicotinoids. In view of the prohibition and restriction of the use of different neonicotinoid pesticides such as imidacloprid, thiamethoxam, clothianidin, and thiacloprid in some countries and regions, dinotefuran has gradually become a major substitute for of the above neonicotinoid pesticides. In EU standards, the MRLs of dinotefuran in different foods are 0.02-8 mg/kg, and in China, the MRLs of dinotefuran are set at 0.02-7 mg/kg.

In order to prevent consumers and beneficial organisms from the hazards and potential impacts of clothianidin and dinotefuran residues, the monitoring of clothianidin and dinotefuran in the environment and agricultural products is of great significance. At present, the detection methods for clothianidin and dinotefuran mainly include instrumental analytical methods and immunoassays. Instrumental analytical methods such as high performance liquid chromatography (HPLC) and ultra-high performance liquid chromatography-tandem mass spectrometry (UPLC-MS) are sensitive and reliable, but precise instrument, professionals, high costs, and complex preparation steps are required. Thus, large-scale rapid on-site analysis cannot be achieved. However, immunoassay methods based on antigen-antibody reactions can realize the rapid detection of pesticide residues without specialized instrument and operators, which are especially suitable for large-scale rapid on-site screening and detection of pesticide residues. These methods can be used as an auxiliary or substitute method for instrumental analytical methods, and have broad application prospects in pesticide residue analysis.

Antibodies are key reaction elements in the immunoassay methods, and quality thereof directly affects the establishment of the immunoassay methods. From existing reports, studies of pesticide antibodies inside and outside of China still mainly focused on traditional antibodies, including polyclonal or monoclonal antibodies, and recombinant fragment antibodies, which have certain limitations in the application of immunoassays. For example, polyclonal antibodies need to be re-immunized after immunized animals are sacrificed by exsanguination, and the uniformity of the antibodies is relatively poor; the preparation of monoclonal antibodies requires long-term dependence on hybridoma cells. If the hybridoma cells have antibody gene mutations or cell lines are lost, monoclonal antibodies will need to be re-developed and the preparation cycle is much longer. With the development of genetic engineering technique, the production of third-generation recombinant antibodies frees the production of antibodies from dependence on animals, ensuring that the same antibody prepared in different batches has high stability and consistency. In another aspect, the objective of antibody “immortality” can be achieved on the basis of obtaining antibody variable region gene sequences. Although studies on recombinant antibodies against pesticides has been reported, most of them are based on the recombinant fragment antibodies such as single-chain antibody and antigen-binding fragment Fab, which cannot completely rival traditional antibodies in terms of biological activity. For example, recombinant fragment antibodies are difficult to be directly coupled with colloidal gold, quantum dots and other labels to form immune probes with stable recognition activity, because of their molecular structures are different from Y-shaped structures of natural antibodies. Therefore, there is an urgent need to develop new recombinant antibodies with reproducible production and stable promotion, which is of great significance for the development and application of immunoassay technology and products thereof for detecting pesticide residue rapidly.

Intact recombinant antibody based on mammalian cell expression is prepared by genetic engineering technique using the antibody heavy and light chain gene sequences in hybridoma cells, peripheral blood lymphocytes, or animal spleen cells as materials. Such recombinant antibody includes amino acid sequence of heavy chain variable and constant regions and light chain variable and constant regions. Moreover, the antibody can be folded and modified correctly, and biological activity thereof is close to that of the natural parent antibody. Since the constant region gene of an antibody is relatively conservative, the sequences of constant regions of antibodies of the same genus and the same type are basically constant, and the sequences are known and published. Thus, when constructing an intact recombinant antibody, as long as a gene of the antibody variable region needs to be accurately amplified, using molecular cloning technology, the variable region gene and the constant region gene are spliced together to obtain an intact gene sequence of the antibody. Compared with recombinant fragment antibodies, the advantages of intact recombinant antibodies are as follows: the structures thereof are the closest to those of natural antibodies, two adjacent antigenic epitopes or molecules can be bound at the same time, and thus high specificity and high affinity to target antigen molecules can be achieved. Therefore, intact recombinant antibodies can be considered to replace traditional parent antibodies in use. Most of the reported intact recombinant antibodies are human-derived antibodies and are used in the medical field. However, there are few reports of intact recombinant antibodies against pesticides and other small molecule pollutants.

SUMMARY

In order to overcome the shortcomings in the prior art, the present disclosure provides a stable production and preparation method of a broad-spectrum intact recombinant antibody that is reproducible, able to be stably promoted, highly sensitive, and capable of simultaneously recognizing small-molecule pesticides clothianidin and dinotefuran.

The present disclosure solves the technical problem with the following technical solution: a variable region sequence of a broad-spectrum antibody against clothianidin and dinotefuran, where a gene encoding a heavy chain variable region has an amino acid sequence shown in SEQ ID NO: 2.

Preferably, the gene encoding a heavy chain variable region may have a nucleotide sequence shown in SEQ ID NO: 1.

Preferably, the gene encoding a light chain variable region may have an amino acid sequence shown in SEQ ID NO: 4.

Preferably, the gene encoding a light chain variable region may have a nucleotide sequence shown in SEQ ID NO: 3.

The present disclosure further provides a broad-spectrum intact recombinant antibody against clothianidin and dinotefuran, including a heavy chain constant region, a heavy chain variable region, a light chain constant region, and a light chain variable region, where a gene encoding the heavy chain variable region has an amino acid sequence shown in SEQ ID NO: 2.

Preferably, the gene encoding the heavy chain variable region may have a nucleotide sequence shown in SEQ ID NO: 1.

Preferably, a gene encoding the light chain variable region may have an amino acid sequence shown in SEQ ID NO: 4.

Preferably, the gene encoding the light chain variable region may have a nucleotide sequence shown in SEQ ID NO: 3.

The present disclosure further provides an antibody expression plasmid, where a nucleotide sequence containing any one of above heavy chain variable regions and a mouse IgG1 heavy chain constant region can express a heavy chain protein of a broad-spectrum intact recombinant antibody against clothianidin and dinotefuran; alternatively, a nucleotide sequence containing the light chain variable region according to any one of claims 3 to 4 and a mouse kappa light chain constant region can express a light chain protein of a broad-spectrum intact recombinant antibody against clothianidin and dinotefuran.

The present disclosure starts from a hybridoma cell line that can stably secrete high-sensitive monoclonal antibodies that simultaneously recognize clothianidin and dinotefuran, and successfully amplifies antibody heavy chain and light chain variable region genes thereof by using 5'RACE technology; with the help of homologous recombination technology, heavy chain and light chain expression vectors are constructed separately, and subjected to liposome-mediated co-transfection into HEK293F cells; an intact recombinant antibody that can simultaneously recognize clothianidin and dinotefuran is prepared through a transient expression system of mammalian cells. Verified by enzyme-linked immunosorbent assay (ELISA) and surface plasmon resonance (SPR), the intact recombinant antibody has high sensitivity and affinity to clothianidin and dinotefuran, and has no obvious cross-reactivity with other structural analogs. Thus, the intact recombinant antibody can be applied to establish immunoassays for simultaneously detecting both clothianidin and dinotefuran, two neonicotinoid pesticides.

Compared with the prior art, the present disclosure has the following advantages: First, the present disclosure is the first to develop an intact recombinant antibody that can simultaneously recognize clothianidin and dinotefuran, and antibody performance thereof is the same as that of a parental monoclonal antibody. Different from parental ascitic monoclonal antibodies, its preparation does not need to rely on processes such as injecting hybridoma cells into the mouse abdomen to prepare ascitic antibodies. Next, the antibody has a higher purity than the ascitic antibodies. Moreover, an antibody gene sequence is obtained during antibody preparation, and a mammalian cell expression system may be used to continuously express the intact recombinant antibody, avoiding the problems of hybridoma cell mutation and death. Finally, unlike those reported recombinant fragment antibodies against pesticides, the intact recombinant antibody has an intact Y-shaped structure, which can be easily modified and labeled like a natural antibody, and can be used to develop stable and rapid immunoassay methods.

BRIEF DESCRIPTION OF THE DRAWINGS

FIG. 1 illustrates the agarose gel electrophoresis results of PCR amplification of a heavy chain variable region gene and a light chain variable region gene using cDNA as a template obtained by reverse transcription based on 5'RACE technology in the present disclosure.

FIG. 2 illustrates the verification of the expression of an intact recombinant antibody in a mammalian cell HEK293F by sodium dodecyl sulfate-polyacrylamide gel electrophoresis (SDS-PAGE) in the present disclosure.

FIG. 3 illustrates ELISA competition curves of an intact recombinant antibody against clothianidin and dinotefuran (pesticide concentrations, from low to high, are 0.20, 0.39, 0.78, 1.56, 3.13, 6.25, 12.5, 25, 50, and 100 ng/mL).

DETAILED DESCRIPTION OF THE EMBODIMENTS

To enable those skilled in the art to better understand the solutions of the present disclosure, the technical solutions in the examples of the present disclosure will be clearly and completely described below in conjunction with the accompanying drawings in the examples of the present disclosure. Obviously, the described examples are only a part of, not all of, the examples of the present disclosure. Based on the examples of the present disclosure, all other examples obtained by those of ordinary skill in the art without creative work shall fall within the protection scope of the present disclosure. Unless otherwise specified, all experimental methods in the examples are conventional.

A broad-spectrum intact recombinant antibody against clothianidin and dinotefuran provided by the present disclosure includes a heavy chain constant region, a heavy chain variable region, a light chain constant region, and a light chain variable region. A heavy chain variable region sequence thereof is a mouse IgG1 heavy chain constant region sequence, and a light chain constant region sequence of the antibody is a mouse kappa light chain constant region sequence.

Preparation of the Intact Recombinant Antibody Against Clothianidin and Dinotefuran 1) Gene Amplification of Variable Region of Monoclonal Antibody Against Clothianidin and Dinotefuran A hybridoma cell line G4 that could secrete antibodies that recognize both clothianidin and dinotefuran was used as a material, and the antibodies secreted thereby were identified as an IgG1 heavy chain and a kappa light chain. Total RNA was extracted from the hybridoma cell line by the Trizol method, and the 5'-end cDNA was amplified by 5'RACE technology. Adapter primers and subtype-specific primers were used to obtain heavy and light chain variable region genes of the antibody. Herein, upstream primers for the heavy and light chains were the adapter primers included in the kit; the specific downstream primer for the heavy chain is CTCAATTTTCTTGTCCACCTTGGT (SEQ ID NO: 5), and the specific downstream primers for the light chain are CTCATTCCTGTTGAAGCTCTTGACAATGGG (SEQ ID NO: 6) and CTCATTCCTGTT-GAAGCTCTTGACGACGGG (SEQ ID NO: 7).

The PCR amplification program was:

| | |
|---|---|
| 95° C. for 45 s | |
| 68° C. for 45 s | 25 cycles |
| 72° C. for 3 min | |

Figure 1:
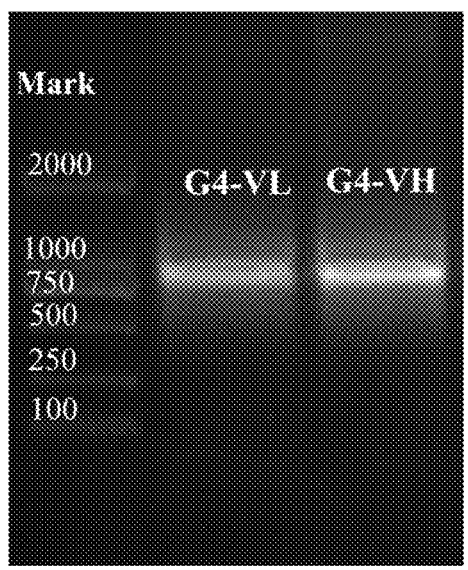

The agarose gel electrophoresis results of PCR amplified products are shown in FIG. 1. Bands containing VH and VL gene fragments were amplified. Purified by a gel extraction kit, purified products were cloned into a pEASY-Blunt vector, transformed, and sequenced. After sequences were aligned to the NCBI database by Blast, VH and VL genes with intact sequences, consistent subtypes, and correct expression cassettes were identified.

G4 heavy chain variable region sequence is as follows:

(SEQ ID NO: 1)
CAGGTGCAGCTGAAGGAGTCAGGACCTGGCCTGGTGGCGCCCTCACAG

AGCCTGTCCATCACTTGCACTATCTCTGGGTTTTCATTAACCAACTAT

GGTGTTCACTGGGTTCGCCAGCCTCCAGGAAAGGGTCTGGAGTGGCTG

GGAGTGATATGGGCTGGTGGAAACACAAATTATAATTCGGCTCTCATG

TCCAGACTGAGCATCAGCAAAGACAACTCCAAGACCCAAGTTTTCTTG

AGAATGAACAGTCTGCAAACTGATGATACAGCCATGTACTACTGTGCC

AGCCCTTTACGCCGCCGCGATATTACTATGGTTTGGACTACTGGGGT

CAAGGAACCTCAGTCACCGTGTCCTCA

The functional heavy chain variable region has a full length of 363 bases. Starting from base 1, the domain encodes 121 amino acids. The functional heavy chain belongs to IGHV2-9*02, and the matching rate of the V region is 96.9%.

The domain is defined by IMGT method, and the specific domain is divided into the following:

| | Domain | | | | | | |
|---|---|---|---|---|---|---|---|
| | FR1 | CDR1 | FR2 | CDR2 | FR3 | CDR3 | FR4 |
| Base sequence | 1 to 75 | 76 to 99 | 100 to 150 | 151 to 171 | 172 to 285 | 286 to 330 | 331 to 363 |

The amino acid sequence of the G4 heavy chain variable region is as follows:

(SEQ ID NO: 2)
QVQLKESGPGLVAPSQSLSITCTISGFSLTNYGVHWVRQPPGKGLEWL

GVIWAGGNTNYNSALMSRLSISKDNSKTQVFLRWINSLQTDDTAMYYC

ASPLRPPRYYYGLDYWGQGTSVTVSS

The amino acid sequence of the G4 light chain variable region is as follows:

(SEQ ID NO: 3)
GATGTTTTGATGACCCAAAGTCCACTCTCCCTGCCTGTCAGTCTTGGA

GATCAAGCCTCCATCTCTTGCAGATCTAGTCAGAGCATTGTTCATAGT

AATGGAAACACCTATTTAGAATGGTACCTGCAGAAACCAGGCCAGTCT

CCAAAGCTCCTGATCTATAAAGTTTCCAACCGATTTTCTGGGGTCCCA

GACAGGTTCAGTGGCAGTGGATCAGGGACAGATTTCATACTCAAGATC

AGTAGAGTGGAGGCTGAGGATCTGGGAGTTTATTACTGCTTTCAAGGC

TCACATGTTCCGTACACGTTCGGAGGGGGGACCAAGCTGGAAATAAAA

The functional light chain variable region has a full length of 336 bases. Starting from base 1, the domain encodes 112 amino acids. The functional light chain belongs to IGKV1-117*01, and the matching rate of the V region is 98.0%.

The domain is defined by IMGT method, and the specific domain is divided into the following:

| | Domain | | | | | | |
|---|---|---|---|---|---|---|---|
| | FR1 | CDR1 | FR2 | CDR2 | FR3 | CDR3 | FR4 |
| Base sequence | 1 to 78 | 79 to 111 | 112 to 162 | 163 to 171 | 172 to 279 | 280 to 306 | 307 to 336 |

The amino acid sequence of the G4 light chain variable region is as follows:

(SEQ ID NO: 4)
DVLMTQSPLSLPVSLGDQASISCRSSQSIVHSNGNTYLEWYLQKPGQS

PKLLIYKVSNRFSGVPDRFSGSGSGTDFILKISRVEAEDLGVYYCFQG

SHVPYTFGGGTKLEIK

2) Construction of Expression Vector

The heavy and light chain variable region genes were ligated to linearized expression vectors pCDNA3.4-Mouse-IgG1 and pCDNA3.4-Mouse-Kappa by homologous recombination, respectively. Herein, the pCDNA3.4-Mouse-IgG1 contained a mouse IgG1 heavy chain constant region gene, and the pCDNA3.4-Mouse-Kappa contained a mouse kappa light chain constant region gene. The heavy/light chain expression vector was transformed into T1 competent cells, cultured under shaking, and sequenced.

3) Expression of the Intact Recombinant Antibody

Figure 2:
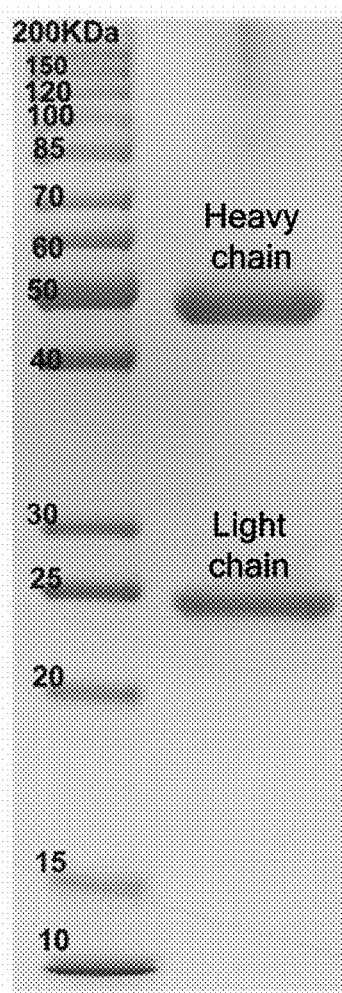

The bacterial suspension corresponding to the correctly sequenced plasmid was cultured and amplified in a large volume, and an EndoFree Plasmid Maxi Kit was used to extract the heavy/light chain expressing plasmid, respectively. In the early stage of transfection, HEK293F cells were resuscitated and cultured in suspension at 120 rpm, 8% $CO_2$, and 37° C. to a density of $3 \times 10^6$ cells/mL; a first passage was carried out with a density of $0.3 \times 10^6$ cells/mL. When the cell density during the first passage was proliferated to $3 \times 10^6$ cells/mL, a second passage was carried out with a density of $0.3 \times 10^6$ cells/mL. When the cell density reached about $3 \times 10^6$ cells/mL, it was ready for transfection and expression. Before transfection, the cells were seeded into a new culture flask with a seeding density of $1.5 \times 10^6$ cells/mL. A heavy chain plasmid, a light chain plasmid, and a liposome transfection reagent were mixed well with culture medium in advance, and allowed to stand at 37° C. for 15 min. The above transfection buffer was added dropwise to the suspension cell culture medium, and shaken well while adding. The transfected cells were cultured in suspension for five days to collect a supernatant. The protein A affinity chromatography column The intact recombinant antibody in the cell supernatant was purified by Protein A affinity chromatography, and the liquid flow rate during the purification was 1 mL/min. The purified antibody was dialyzed overnight with 0.01 M PBS solution. After dialysis, the antibody concentration was determined to be 3 mg/mL, which was verified by SDS-PAGE (FIG. 2).

Characterization of the Intact Recombinant Antibody

1) Establishment of Heterologous Indirect Competitive ELISA for the Intact Recombinant Antibody In the early stage of preparation of parental ascitic monoclonal antibodies, a difference in sensitivity was compared between the homologous indirect competitive ELISA (coating antigen was clothianidin-OVA) and the heterologous indirect ELISA (coating antigens were thiacloprid-OVA and imidaclothiz-OVA). It was found that the sensitivity of the ELISA method was the highest when the thiacloprid-OVA was used as a heterologous coating antigen. Therefore, in the present disclosure, the heterologous indirect competitive ELISA using thiacloprid-OVA as the coating antigen was used to evaluate the sensitivity and specificity of the intact recombinant antibody against clothianidin and dinotefuran. A 96-well plate was coated with the thiacloprid-OVA as the heterologous coating antigen; subsequently, ELISA was performed using a rabbit anti-mouse IgG-HRP as a detection antibody, tetramethylbenzidine (TMB) as a reaction substrate, and clothianidin, dinotefuran, and other structural analog pesticide standards as analytes.

1) Sensitivity of Intact Recombinant Antibody ($IC_{50}$)

Figure 3:
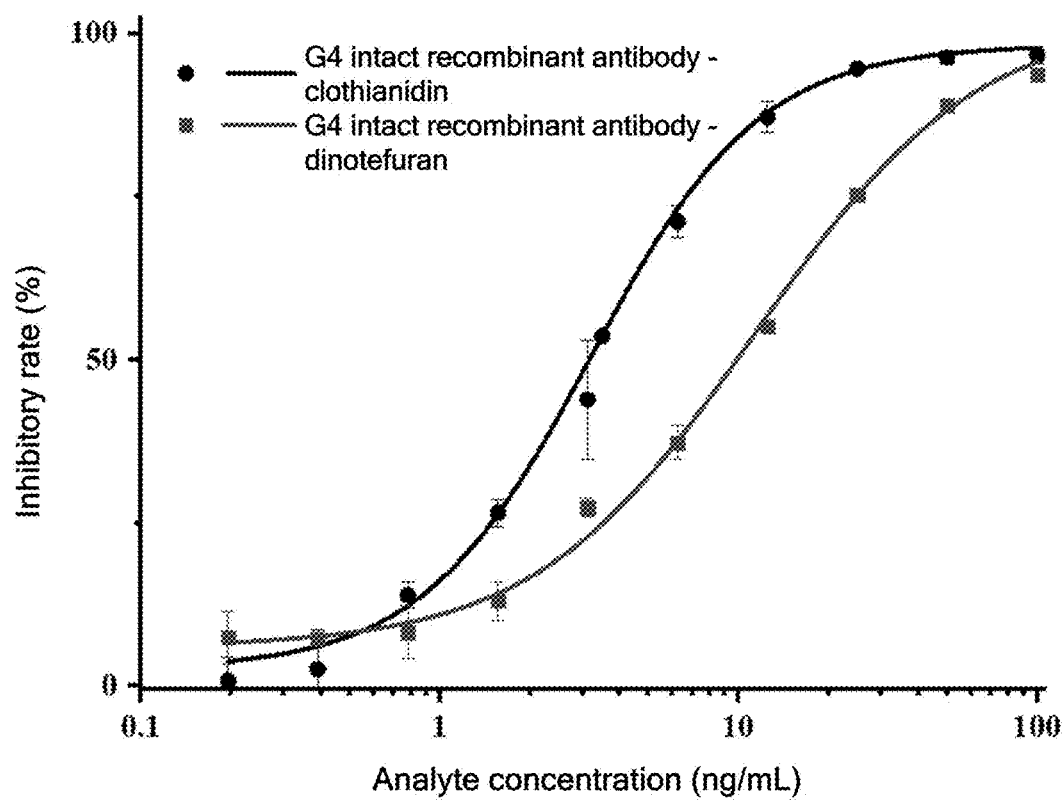

According to the inhibitory rate and the concentrations of clothianidin and dinotefuran, standard curves were plotted and established (FIG. 3), and the median inhibitory concentrations ($IC_{50}$) and linear ranges ($IC_{20}$ to $IC_{80}$) of clothianidin and dinotefuran were calculated, respectively. Herein, the $IC_{50}$ of clothianidin toward the intact recombinant antibody was 5.22 ng/mL, with a linear range of 1.08-15.06 ng/mL; the $IC_{50}$ of dinotefuran toward the intact recombinant antibody was 10.66 ng/mL, with a linear range of 3.78-30.03 ng/mL.

2) Specificity of the Intact Recombinant Antibody

In the present disclosure, the specificity of the antibody was evaluated by detecting the cross-reactivity with eight common neonicotinoid insecticides. The data of heterologous indirect competitive ELISA showed that the intact recombinant antibody prepared in the present disclosure could specifically recognize clothianidin and dinotefuran, but had no apparent cross-reactivity with imidacloprid, thiacloprid, acetamiprid, imidaclothiz, thiamethoxam, and nitenpyram ($IC_{50}>1,000$ ng/mL, cross-reactivity <0.5%); the prepared intact recombinant antibody could be used for specific analysis of clothianidin and dinotefuran.

3) Kinetic Surface Plasmon Resonance (SPR) Characterization of the Intact Recombinant Antibody In the present disclosure, the affinity of the intact recombinant antibody to a target analyte was detected by Biacore T200.

Kinetic determination analyzed the affinity of the intact recombinant antibody to clothianidin or dinotefuran at a series of analyte concentrations. The results showed that the affinity of the intact recombinant antibody to clothianidin was $7.96 \times 10^{-9}$ M and the affinity thereof to dinotefuran was $7.56 \times 10^{-9}$ M. Therefore, it was found that the intact recombinant antibody prepared in the present disclosure had a high affinity to both clothianidin and dinotefuran.

What is claimed is:

1. A broad-spectrum intact recombinant antibody against clothianidin and dinotefuran, comprising a heavy chain constant region, a heavy chain variable region comprising an amino acid sequence of SEQ ID NO:2, a light chain constant region, and a light chain variable region comprising an amino acid sequence of SEQ ID NO: 4.

2. The broad-spectrum intact recombinant antibody against clothianidin and dinotefuran according to claim 1, wherein a gene encoding the heavy chain variable region has a nucleotide sequence shown in SEQ ID NO: 1.

3. The broad-spectrum intact recombinant antibody against clothianidin and dinotefuran according to claim 1, wherein a gene encoding the light chain variable region has a nucleotide sequence shown in SEQ ID NO: 3.

4. The broad-spectrum intact recombinant antibody against clothianidin and dinotefuran according to claim 1, wherein a gene encoding the heavy chain variable region has a nucleotide sequence shown in SEQ ID NO: 1 and a gene encoding the light chain variable region has a nucleotide sequence shown in SEQ ID NO: 3.

5. An expression plasmid for expressing the broad-spectrum intact recombinant antibody against clothianidin and dinotefuran of claim 1.

6. The expression plasmid of claim 5, wherein a gene encoding the heavy chain variable region has a nucleotide sequence shown in SEQ ID NO: 1.

7. The expression plasmid of claim 5, wherein a gene encoding the light chain variable region has a nucleotide sequence shown in SEQ ID NO:3.

8. The expression plasmid of claim 5, wherein a gene encoding the heavy chain variable region has a nucleotide sequence shown in SEQ ID NO: 1 and a gene encoding the light chain variable region has a nucleotide sequence shown in SEQ ID NO: 3.

9. The expression plasmid of claim 5, comprising a mouse IgG1 heavy chain constant region nucleotide sequence, the heavy chain variable region nucleotide sequence shown in SEQ ID NO: 1, a mouse kappa light chain constant region nucleotide sequence and a light chain variable region nucleotide sequence shown in SEQ ID NO: 3, wherein the nucleotide sequence of the heavy chain constant region and the heavy chain variable region is capable of expressing the heavy chain protein of the broad-spectrum intact recombinant antibody against clothianidin and dinotefuran, and the nucleotide sequence of the light chain constant region and the light chain variable region is capable of expressing the light chain protein of the broad-spectrum intact recombinant antibody against clothianidin and dinotefuran.

\* \* \* \* \*

SEQUENCE LISTING

```
<160> NUMBER OF SEQ ID NOS: 7

<210> SEQ ID NO 1
<211> LENGTH: 363
<212> TYPE: DNA
<213> ORGANISM: Artificial Sequence
<220> FEATURE:
<223> OTHER INFORMATION: G4 heavy chain variable region sequence

<400> SEQUENCE: 1
caggtgcagc tgaaggagtc aggacctggc ctggtggcgc cctcacagag cctgtccatc        60
acttgcacta tctctgggtt ttcattaacc aactatggtg ttcactgggt tcgccagcct       120
ccaggaaagg gtctggagtg gctgggagtg atatgggctg gtggaaacac aaattataat       180
tcggctctca tgtccagact gagcatcagc aaagacaact ccaagaccca gtttttcttg       240
```

```
agaatgaaca gtctgcaaac tgatgataca gccatgtact actgtgccag cccttttacgg    300 ccgccgcgat attactatgg tttggactac tggggtcaag gaacctcagt caccgtgtcc    360
tca                                                                  363
```

<210> SEQ ID NO 2
<211> LENGTH: 121
<212> TYPE: PRT
<213> ORGANISM: Artificial Sequence
<220> FEATURE:
<223> OTHER INFORMATION: amino acid sequence of the G4 heavy chain
      variable region

<400> SEQUENCE: 2

```
Gln Val Gln Leu Lys Glu Ser Gly Pro Gly Leu Val Ala Pro Ser Gln
1               5                   10                  15

Ser Leu Ser Ile Thr Cys Thr Ile Ser Gly Phe Ser Leu Thr Asn Tyr
            20                  25                  30

Gly Val His Trp Val Arg Gln Pro Pro Gly Lys Gly Leu Glu Trp Leu
        35                  40                  45

Gly Val Ile Trp Ala Gly Gly Asn Thr Asn Tyr Asn Ser Ala Leu Met
    50                  55                  60

Ser Arg Leu Ser Ile Ser Lys Asp Asn Ser Lys Thr Gln Val Phe Leu
65                  70                  75                  80

Arg Met Asn Ser Leu Gln Thr Asp Asp Thr Ala Met Tyr Tyr Cys Ala
                85                  90                  95

Ser Pro Leu Arg Pro Pro Arg Tyr Tyr Tyr Gly Leu Asp Tyr Trp Gly
            100                 105                 110

Gln Gly Thr Ser Val Thr Val Ser Ser
        115                 120
```

<210> SEQ ID NO 3
<211> LENGTH: 336
<212> TYPE: DNA
<213> ORGANISM: Artificial Sequence
<220> FEATURE:
<223> OTHER INFORMATION: G4 light chain variable regionsequence

<400> SEQUENCE: 3

```
gatgttttga tgacccaaag tccactctcc ctgcctgtca gtcttggaga tcaagcctcc     60
atctcttgca gatctagtca gagcattgtt catagtaatg gaaacaccta tttagaatgg    120
tacctgcaga aaccaggcca gtctccaaag ctcctgatct ataaagtttc caaccgattt    180
tctggggtcc cagacaggtt cagtggcagt ggatcaggga cagatttcat actcaagatc    240
agtagagtgg aggctgagga tctgggagtt tattactgct ttcaaggctc acatgttccg    300
tacacgttcg gagggggac caagctggaa ataaaa                               336
```

<210> SEQ ID NO 4
<211> LENGTH: 112
<212> TYPE: PRT
<213> ORGANISM: Artificial Sequence
<220> FEATURE:
<223> OTHER INFORMATION: amino acid sequence of the G4 light chain
      variable region

<400> SEQUENCE: 4

```
Asp Val Leu Met Thr Gln Ser Pro Leu Ser Leu Pro Val Ser Leu Gly
1               5                   10                  15
```

```
Asp Gln Ala Ser Ile Ser Cys Arg Ser Ser Gln Ser Ile Val His Ser
             20                  25                  30

Asn Gly Asn Thr Tyr Leu Glu Trp Tyr Leu Gln Lys Pro Gly Gln Ser
         35                  40                  45

Pro Lys Leu Leu Ile Tyr Lys Val Ser Asn Arg Phe Ser Gly Val Pro
     50                  55                  60

Asp Arg Phe Ser Gly Ser Gly Ser Gly Thr Asp Phe Ile Leu Lys Ile
65                  70                  75                  80

Ser Arg Val Glu Ala Glu Asp Leu Gly Val Tyr Tyr Cys Phe Gln Gly
                 85                  90                  95

Ser His Val Pro Tyr Thr Phe Gly Gly Gly Thr Lys Leu Glu Ile Lys
             100                 105                 110

<210> SEQ ID NO 5
<211> LENGTH: 24
<212> TYPE: DNA
<213> ORGANISM: Artificial Sequence
<220> FEATURE:
<223> OTHER INFORMATION: the specific downstream primer for the heavy
      chain

<400> SEQUENCE: 5
ctcaattttc ttgtccacct tggt                                            24

<210> SEQ ID NO 6
<211> LENGTH: 30
<212> TYPE: DNA
<213> ORGANISM: Artificial Sequence
<220> FEATURE:
<223> OTHER INFORMATION: the specific downstream primers for the light
      chain-1

<400> SEQUENCE: 6
ctcattcctg ttgaagctct tgacaatggg                                      30

<210> SEQ ID NO 7
<211> LENGTH: 30
<212> TYPE: DNA
<213> ORGANISM: Artificial Sequence
<220> FEATURE:
<223> OTHER INFORMATION: the specific downstream primers for the light
      chain-2

<400> SEQUENCE: 7
ctcattcctg ttgaagctct tgacgacggg                                      30
```